US007020561B1

(12) United States Patent
McLoughlin et al.

(10) Patent No.: US 7,020,561 B1
(45) Date of Patent: Mar. 28, 2006

(54) METHODS AND SYSTEMS FOR EFFICIENT COMPARISON, IDENTIFICATION, PROCESSING, AND IMPORTING OF GENE EXPRESSION DATA

(75) Inventors: Kevin McLoughlin, Oakland, CA (US); Francois Collin, Berkeley, CA (US); Victor M. Markowitz, Albany, CA (US); Thodoros Topaloglou, Toronto (CA); Alexandros Athanasopoulos, Oakland, CA (US)

(73) Assignee: Gene Logic, Inc., Gaithersburg, MD (US)

( * ) Notice: Subject to any disclaimer, the term of this patent is extended or adjusted under 35 U.S.C. 154(b) by 68 days.

(21) Appl. No.: 10/212,445

(22) Filed: Aug. 5, 2002

Related U.S. Application Data

(63) Continuation-in-part of application No. 10/096,645, filed on Mar. 14, 2002, and a continuation-in-part of application No. 10/090,144, filed on Mar. 5, 2002, and a continuation-in-part of application No. 09/862,424, filed on May 23, 2001.

(60) Provisional application No. 60/309,895, filed on Aug. 6, 2001, provisional application No. 60/309,908, filed on Aug. 6, 2001, provisional application No. 60/309,814, filed on Aug. 6, 2001, provisional application No. 60/275,465, filed on Mar. 14, 2001, provisional application No. 60/325,776, filed on Mar. 5, 2001, provisional application No. 60/206,571, filed on May 23, 2000.

(51) Int. Cl.
*G06F 7/06* (2006.01)
*G06F 17/30* (2006.01)
*G06F 7/00* (2006.01)

(52) U.S. Cl. .............................. 702/19; 702/20; 703/2; 707/100; 707/101; 707/102

(58) Field of Classification Search .................. 702/19, 702/20; 703/2; 707/100, 101, 102
See application file for complete search history.

(56) References Cited

U.S. PATENT DOCUMENTS

| 5,495,606 | A | 2/1996 | Borden et al. |
| 5,569,580 | A | 10/1996 | Young |
| 5,589,337 | A | 12/1996 | Farr |
| 5,634,053 | A | 5/1997 | Noble et al. |
| 5,692,107 | A | 11/1997 | Simoudis et al. |
| 5,702,915 | A | 12/1997 | Miyamoto |
| 5,736,354 | A | 4/1998 | Fielden et al. |
| 5,769,074 | A | 6/1998 | Barnhill et al. |
| 5,787,425 | A | 7/1998 | Bigus |
| 5,811,231 | A | 9/1998 | Farr et al. |
| 5,835,755 | A | 11/1998 | Stellwagen, Jr. |
| 5,873,083 | A | 2/1999 | Jones et al. |
| 5,933,818 | A | 8/1999 | Kasravi et al. |
| 6,109,776 | A | 8/2000 | Haas |
| 6,128,608 | A | 10/2000 | Barnhill |
| 6,160,105 | A | 12/2000 | Cunningham et al. |
| 6,185,561 | B1 | 2/2001 | Balaban et al. |
| 6,189,013 | B1 | 2/2001 | Maslyn et al. |
| 6,203,987 | B1 | 3/2001 | Friend et al. |
| 6,223,186 | B1 | 4/2001 | Rigault et al. |
| 6,308,170 | B1 | 10/2001 | Balaban |
| 6,309,822 | B1 | 10/2001 | Fodor et al. |
| 6,408,308 | B1 | 6/2002 | Maslyn et al. |
| 6,418,382 | B1 | 7/2002 | Rothberg et al. |
| 6,427,141 | B1 | 7/2002 | Barnhill |
| 6,453,241 | B1 | 9/2002 | Bassett, Jr. et al. |
| 6,470,277 | B1 | 10/2002 | Chin et al. |
| 6,484,183 | B1 | 11/2002 | Balaban et al. |
| 6,532,462 | B1 | 3/2003 | Balaban et al. |

FOREIGN PATENT DOCUMENTS

WO    PCT/US02/07727    3/2002

OTHER PUBLICATIONS

Eppig et al. METHODS: A Companion to Methods in Enzymology (1998) vol. 14, pp. 179-190.*
Bassett, D., Jr., et al., "Gene Expression Informatics—It's All in Your Mine," Nature Genetics Supplement, vol. 21, Jan. 1999, pp. 51-55.
Canfield, K., et al., "Mapping XML Documents into Databases: A Data-Driven Framework for Bioinformatic Data Interchange," AMIA Symposium, Nov. 2000, pp. 121-125.
Duggan, D., et al., "Expression Profiling Using cDNA Microarrays," Nature Genetics Supplement, vol. 21, Jan. 1999, pp. 10-14.
Ermolaeva, O., et al., "Data Management and Analysis for Gene Expression Arrays," Nature Genetics Supplement, vol. 20, Sep. 1998, pp. 19-23.
Rebhan, M., et al., "GeneCards: A Novel Functional Genomics Compendium with Automated Data Mining and Query Reformulation Support," Bioinformatics, vol. 14, No. 8, 1998, pp. 656-664.
Tarczy-Hornoch, P., et al., "GeneClinics: A Hybrid Text/Data Electronic Publishing Model Using XML Applied to Clinical Genetic Testing," J. Amer. Med. Inform. Assoc., vol. 7, No. 3, 2000, pp. 267-276.

* cited by examiner

*Primary Examiner*—Marjorie A. Moran
*Assistant Examiner*—Lori A. Clow
(74) *Attorney, Agent, or Firm*—Eleanor M. Musick; Procopio Cory Hargreaves & Savitch LLP

(57) ABSTRACT

The present invention provides systems and methods for analyzing gene expression, gene annotation, and sample information in a relational format supporting efficient exploration and analysis, including comparative differential expression analysis, expression pattern matching, and mapping of external attributes or identifiers to internal representations of gene fragments or samples.

33 Claims, 6 Drawing Sheets

METHODS AND SYSTEMS FOR EFFICIENT COMPARISON, IDENTIFICATION, PROCESSING, AND IMPORTING OF GENE EXPRESSION DATA

CROSS-REFERENCE TO RELATED APPLICATIONS

This application claims priority to U.S. provisional application Ser. Nos. 60/309,895; 60/309,908; and 60/309,814, all filed on Aug. 6, 2001, and is a continuation-in-part of each of U.S. application Ser. No. 10/096,645, filed Mar. 14, 2002, published as Publ. No. U.S. 2003/0009295, which claims priority to provisional application Ser. No. 60/275,465, filed Mar. 14, 2001, and is a continuation in part of U.S. application Ser. No. 10/090,144, filed Mar. 5, 2002, published as Publ. No. U.S. 2003/0171876, which claims priority to provisional application Ser. No. 60/325,776, filed Mar. 5, 2001, and is a continuation in part of U.S. application Ser. No. 09/862,424, filed May 23, 2001, published as Publ. No. U.S. 2003/0100999, which claims priority to provisional application Ser. No. 60/206,571, filed May 23, 2000. This application is related to PCT application Ser. No. US02/19877, filed in the U.S. Receiving Office on Jun. 24, 2002, published as International Publ. No. WO 03/001335, which claims priority to provisional application Ser. No. 60/299,741, filed Jun. 22, 2001. Each of the related applications is incorporated herein by reference in its entirety for all purposes.

FIELD OF THE INVENTION

The present invention relates generally to systems and methods for processing gene expression data and more specifically to efficient identification of differentially expressed gene sets, utilization of contrast analysis to identify genes with specific patterns of expression, and importing gene sets and sample sets from lists of external attributes.

BACKGROUND OF THE INVENTION

The study of gene expression brings valuable information to the researcher about cellular function that can be applied directly to drug discovery and development. Devices and computer systems and methods have been developed for collecting information about gene expression or expressed sequence tag (EST) expression in large numbers of tissues.

DNA microarrays are glass or nylon chips or substrates containing arrays of DNA samples, or "probes", which can be used to analyze gene expression. A fluorescently labeled nucleic acid is brought into contact with the microarray and a scanner generates an image file indicating the locations within the microarray at which the labeled nucleic acids are bound. Based on the identity of the probes at these locations, information such as the monomer sequence of DNA or RNA can be extracted. By profiling gene expression, transcriptional changes can be monitored through organ and tissue development, microbiological infection, and tumor formation. The robotic instruments used to spot the DNA samples onto the microarray surface allow thousands of samples to be simultaneously tested. This high-throughput approach increases reproducibility and production.

Microarray technologies enable the generation of vast amounts of gene expression data. Effective use of these technologies requires mechanisms to manage and explore large volumes of primary and derived (analyzed) gene expression data. Furthermore, the value of examining the biological meaning of the information is enhanced when set in the context of sample profiles and gene annotation data. The format and interpretation of the data depend strongly on the underlying technology. Hence, exploring gene expression data requires mechanisms for integrating gene expression data across multiple platforms and with sample and gene annotations.

The GeneChip® probe array of Affymetrix, Inc. (Santa Clara, Calif.) is one example of a widely-adopted microarray technology that provides for the high-volume screening of samples for gene expression. Affymetrix also offers a series of software solutions for data collection, conversion to AADM™ ("Affymetrix Analysis Data Model") database format, data mining, and a multi-user laboratory information management system ("LIMS"). LIMS is a microarray data management package for users who are generating large quantities of GeneChip® probe array data. Data are published to an AADM-standard database that can be searched by mining tools that are AADM-compliant. The Affymetrix technology has become one of the standards in the field, and large databases of gene expression data generated using this technology, along with associated information, have been assembled and are publicly-available for data mining by pharmaceutical, biotechnology, and other researchers and clinicians. The researchers may wish to utilize a specific analysis and visualization tool, or to use multiple such tools for efficient identification and comparison of gene expression data.

For example, toxicology experiments may involve administration of a toxin to a set of laboratory animals and then sampling the animals at various time intervals following introduction of the toxin. There may be groups of animals that are sampled at three, six, and twenty-four hours after toxin administration, as well as some untreated animals. A researcher may also have previously observed an indication that a gene is involved in a toxic response and also that its expression level increases or decreases in a certain pattern at the time intervals sampled. In order to find other genes that may be involved in the same toxic response, the researcher may wish to identify other genes that demonstrate that same pattern of expression across these groups of samples corresponding to these time intervals.

It is conventional to run three to ten or more replicate experiments for each set of experimental conditions and/or time points. For example, seven animals may be sampled at three hours, six hours, and twenty-four hours after toxin administration. It is desirable to utilize the information derived from these replica experiments to find genes that consistently have a specified pattern of expression over a given set of experimental conditions and sampling times; that is, genes whose expression level varies very little within a group of samples that are replicates, but whose expression level varies greatly between samples corresponding to different experimental conditions or time points, all according to the pattern specified by the user. Such analytical tools have not been previously available.

In another example, there have been past attempts to develop an efficient analysis of gene expression data, such as, for example, clustering, of which there are many subtypes that are well known to those skilled in the art. One method, referred to as gene signature differential, identifies genes which have detectable expression in a minimum fraction of samples in one sample set and do not have detectable expression in at least another fraction of samples in a second sample set. For example, a comparison of samples in the first sample set may be typically drawn from disease or toxin-treated tissues while samples for the second sample set may be normal or untreated tissue.

Gene signature differential is based on another analysis method known as gene signature. Gene signature analysis identifies two sets of genes, given a set of samples and two user-specified threshold fractions P and A. The two gene sets generated by the gene signature are referred to as the present set and the absent set. The present set includes genes that are present, or have detectable expression in at least P percent of samples in the sample set; similarly, the absent set includes genes called absent (not having detectable expression) in at least A percent of samples. The conventional method of performing a gene signature differential is to run two gene signatures, take those gene signature sets, and compute the set intersections, the present set from one gene signature intersected with the absent set from the other signature. Next, another set is computed that includes the absent set from gene signature number one intersected with the present set from gene signature number two. Accordingly, this method includes the preliminary step of computing the two present gene sets and absent gene sets, and such a method is inefficient.

Accordingly, there is a need for methods and systems for the efficient comparison, identification, and processing of gene expression data.

SUMMARY OF THE INVENTION

The present invention satisfies the above-described needs by providing systems and methods for the efficient comparison, identification, and importing of gene expression data derived from DNA probe array experiments. One aspect of the present invention is to prioritize genes that are being profiled through these DNA probe array gene expression experiments to determine how closely the pattern of expression of each gene under analysis matches a pattern of expression a user is interested in over a set of groups of samples.

A contrast analysis tool according to an exemplary embodiment of the present invention applies a statistical method of contrast analysis in order to prioritize a set of genes according to how well the set's pattern of expression under different experimental conditions follows a group of user-specified patterns. The prioritization is performed based on the computation of a t-like statistic for each gene tested, using expression data derived from high-density oligonucleotide array experiments. The invention addresses the problem of identifying genes whose levels of expression increase or decrease in a pattern previously known to be related to some biological process, such as disease, toxicity, or drug response.

Another preferred embodiment of the present invention includes a method and system for improving existing methods for computing gene signature differentials. Intersection sets computed using gene signature differential analysis usually include a very small fraction of the total set of genes that are profiled in gene chip experiments. For example, many experiments on human tissue involve profiling expression on 62,000 genes simultaneously, however, the gene signature differential sets contain typically 20 to 30 genes out of those 62,000, which is a very small subset. An embodiment of the present invention bypasses the calculation of the original present and absent sets for each input sample set by using a reverse calculation to determine whether each gene does not belong to an intersection set rather than attempting to determine whether each gene belongs in an intersection set.

Another preferred embodiment of the invention provides a tool for querying a gene sequence database using multiple queries by permitting a user to create a file containing a list of the multiple attributes for the query. The gene query tool permits a user to import genes or samples by attribute value, providing a mechanism for creating gene sets or sample sets that correspond to some set of values for some attribute or identifier associated with samples or genes in the database. A user may display a dialog box that shows a tree view of all the different attributes stored in the database for genes or samples, from which the user may select an attribute. The dialog box may also provide a place for the user to navigate to or enter a name of a file containing potential values for the selected attribute. The gene query tool permits a user to invoke the tool, to use a dialog window, to navigate the tree of choices and to select the attribute by which one wishes to import. In a preferred embodiment, the selection may be the GenBank accession attribute. The user may select a file containing a list of GenBank accession numbers and request import of the corresponding gene fragments. The query tool generates the necessary database query (or queries) to capture all the gene fragments in the database that match any of the listed accession numbers and to return the results to the user.

It will be appreciated that GenBank accession numbers are merely one of the attributes by which the database can be queried. One may select any gene attribute in the database and request all genes that match any of the values that specify the attributes.

DETAILED DESCRIPTION OF THE INVENTION

An exemplary environment for methods and systems according to the present invention includes an enterprise-wide software platform for gene expression research. The exemplary environment includes a system that provides integration, management, and analysis of large amounts of Affymetrix® GeneChip®-based gene expression data from different sources. The system includes capabilities for capturing and analyzing associated clinical and experimental information. The system accepts data from the major Affymetrix® GeneChip® probe array types across various species and can accommodate custom chips.

Figure 1:
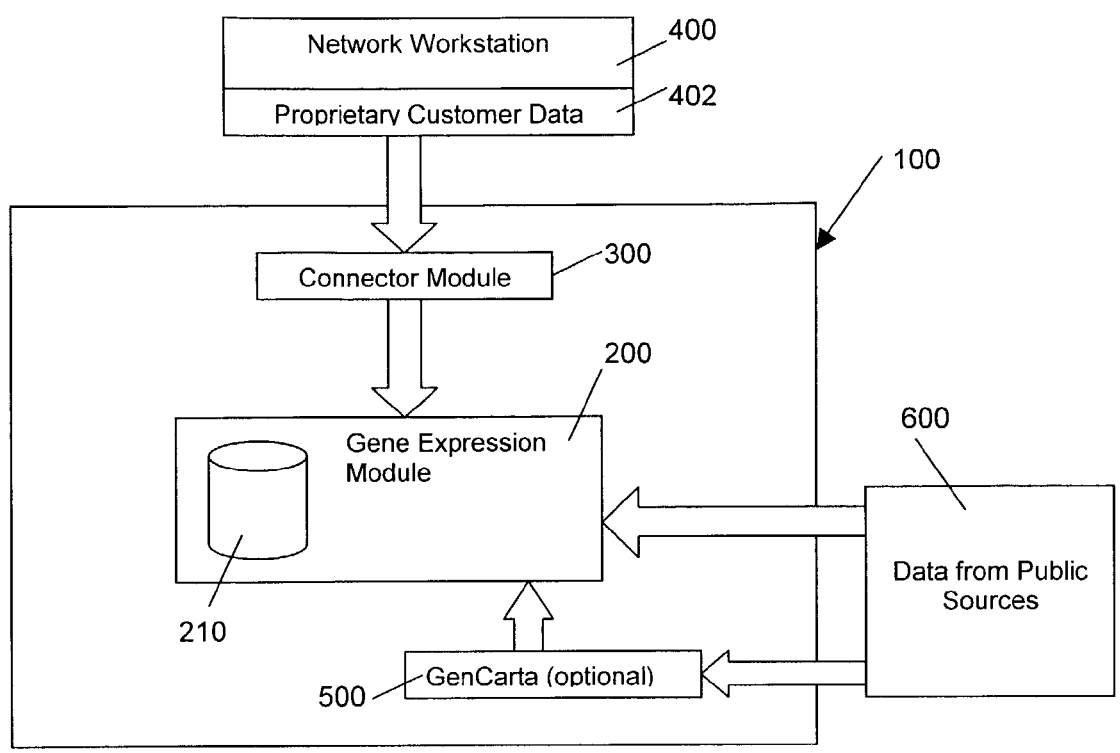
FIG. 1 is a block diagram of a top level view of an exemplary software platform for exemplary embodiments of methods and systems according to the present invention.

As illustrated in FIG. 1, the exemplary software platform 100 comprises a gene expression module 200, a connector module 300, and a user interface 400 comprising a network workstation, which includes means for entry of customer data 402. Optional module 500 provides access to the GenCarta™ transcriptome database system from Compugen, Ltd. (Tel Aviv, Israel). Both gene expression module 200 and the GenCarta system include means for extraction of data from public sources 600 such as Genbank, SwissProt, LocusLink, Unigene, KEGG, SPAD, PubMed, HUGO, OMIM, and GeneCard. This list is not intended to be exhaustive, and other sources, both private and public, may be used.

Figure 2:
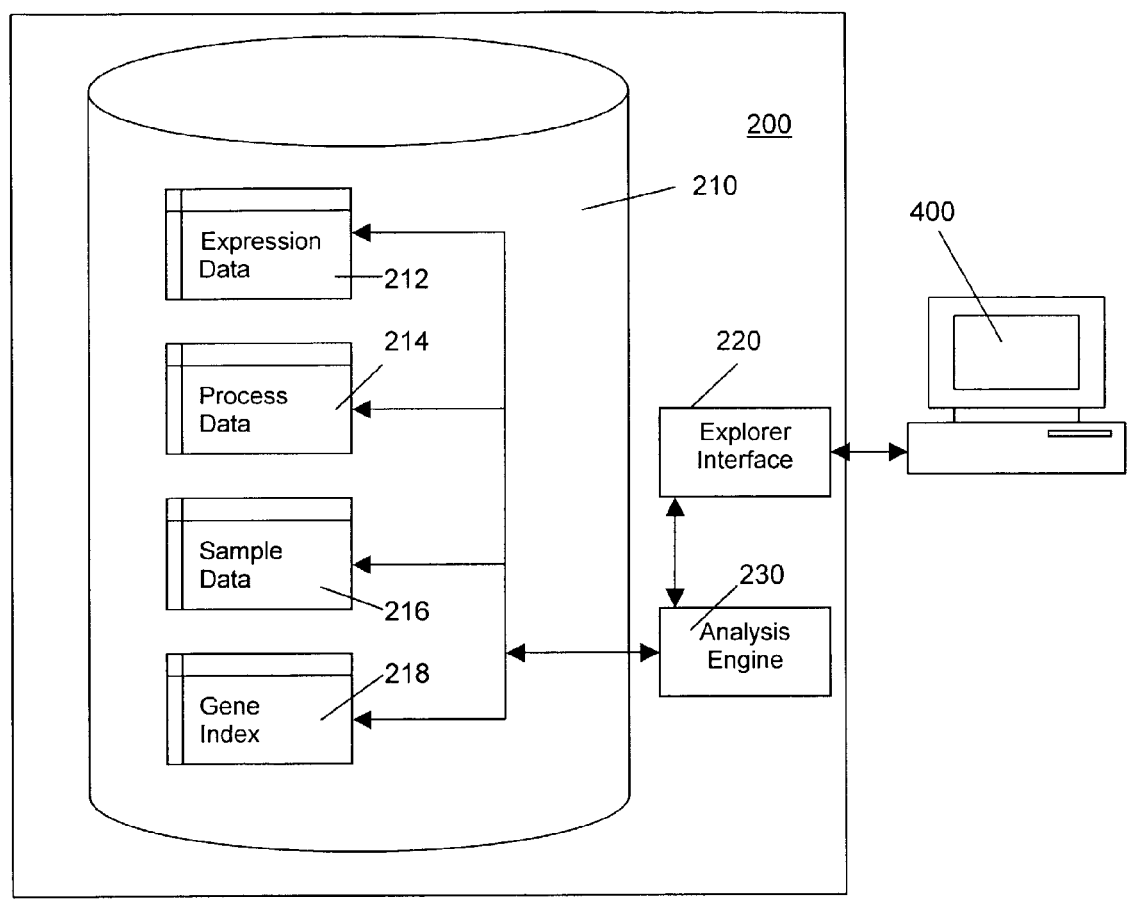
FIG. 2 is a block diagram of a gene expression module of the exemplary software platform of FIG. 1.

Referring now to FIG. 2, gene expression module 200, available commercially as the GeneExpress® software system, comprises a three-tier client-server application with several sub-components. The data warehouse 210 is an Oracle®-based warehouse that maintains a large collection of data. Data warehouse 210 comprises summarized and curated gene expression data, integrated with sample and gene annotation data, and provides support for effective data exploration and mining. The data in the collection are partitioned into several databases. The gene expression database 212 contains a large volume of gene expression data in GATC/AADM compliant formats. Process database 214 stores information which characterizes and is related to the gene expression data in database 212, including information on experiment set grouping, QC data, and experimental conditions under which the gene expression data was generated. Sample database 216 stores sample or clinical data that include bio-samples, donors, and standardized terms that describe the samples. Sample data can be organized by static controlled vocabulary classes such as type, species, organ, clinical and demographic data, lifestyle factor, treatment outcome, etc., or can be organized into experimental study groups, SNOMED disease term and code, SNOMED organ term and code, etc. Templates are preferably used to standardize the organization of the sample data.

Gene index database 218 stores annotations which can be used to uniquely identify the gene expression data stored in database 212. The gene index database 218 links each gene fragment with existing annotations of the gene contained in public databases such as Genbank, SwissProt, LocusLink, Unigene, KEGG, SPAD, PubMed, HUGO, OMIM, and GeneCard, all of which are known in the art. In linking the gene fragment with existing databases, the inventive system maintains recognized biological meaning and identity, thus avoiding redundancy, ambiguity, or errors. The gene fragments can also be linked in gene index database 218 to chromosomes and to biological pathways such as the protein signaling pathways available from BioCarta, Inc. (San Diego, Calif.).

Explorer interface 220 is a Java-based application that provides the end-user interface to the system for user interface 400. User access to gene expression module 200 is limited to entry of search queries and a read-only function, which allows the user to view data stored in the data warehouse 210 that is identified as the result of the search. The explorer interface 220 provides analysis and visualization tools, and also provides seamless integration with other popular tools. Explorer interface 220 also keeps track of a user's research and analysis activities, including selected sample or gene sets and analysis results, for later retrieval through a workspace manager.

Analysis engine 230, also referred to as the "Run time engine" or "RTE", is a server-based application that is optimized for performing the core functional and computational duties within gene expression module 200. Analysis engine 230 communicates and links between the explorer interface 220 and the data warehouse 210 while providing the primary power for all complex analysis tasks.

User interface 400 provides tools allowing users to extract subsets of the gene expression data stored in the data warehouse 210, analyze them and display the results. These tools enable users to answer questions such as: 1) which genes are consistently expressed or repressed in a group of tissue samples?; 2) what genes are more highly expressed in one organ or tissue than in another? How do their expression levels vary with age, in different diseases, or in the presence of different medications?; 3) which genes are always expressed in one tissue and absent in another? Which are exclusively expressed in a given tissue type?; 4) what metabolic pathways are affected by a particular drug or toxin, in terms of the expression levels of the genes involved in the pathway? System tools provide a number of options for displaying expression data and analysis results including tabular displays in the user's Web browser, export to spreadsheets, graphical visualizations, metabolic pathway map displays, statistical analysis and simple tab-delimited text for export to third party tools.

The inputs used by the system tools to perform analyses include sample sets and gene sets. A sample set is a list of tissue samples for which gene expression data is stored in the database. Users define sample sets for analysis by specifying a combination of query criteria applied to the clinical data in the sample database 216. Each criterion consists of an attribute such as "Biosample: tissue category" and a value, e.g., "Normal" or "Malignant". A gene set is a list of DNA fragments or probe sets for which there is gene expression data in the database. Users may define gene sets by specifying a combination of query criteria applied to the gene index database 218.

Over time, system users will develop a large number of datasets. These datasets are handled by a workspace manager, which is a centralized repository of sample sets, gene sets and analysis results organized into user-defined projects and folders. Access to the user's datasets can be password limited. The workspace is loaded with publicly accessible read-only gene sets and sample sets corresponding to commonly performed queries such as genes involved in each metabolic pathway and samples classified by organ or tissue type. These gene sets and sample sets may be copied to a user's own project folder and may be edited or merged with other gene sets and sample sets.

The improvements disclosed herein are intended for incorporation and interaction with the gene expression module 200 and do not require the inclusion of connector module 300 to achieve the desired function. Accordingly, with reference to FIG. 1, the connector module 300 and the proprietary customer data 402 can be omitted, with a user interface (e.g., network workstation 400) providing direct access to gene expression module 200 for querying and viewing of results. Nonetheless, the following provides a brief description of connector module 300, which provides the advantage of permitting addition of proprietary customer data 402 to the existing data in the data warehouse 210 for query and analysis based on the combined data record. Thus, the improved method and systems disclosed herein can be performed on data that is pre-existing in the data warehouse 210, or on data that is the combination of imported customer data and pre-existing data when connector module 300 is included.

Connector module 300 provides means for a user to load more than one source of gene expression, and sample information in the data warehouse 210 of gene expression module 200. In particular, connector module 300 permits a system user to load the user's expression data and sample data from external files into the data warehouse for comparison or combination with a pre-existing, internally-stored set of data, i.e., the data already existing in data warehouse 210. To facilitate distinction between the different data sources, the latter data may be referred to as the "pre-existing data" while the user's data will be referred to as "customer data". Connector module 300 provides an interactive interface to manually add and edit sample data through a sample data manager, which provides validation and migration of sample data from external files into the system. An XML sample migration template facilitates preparation of sample data for migration. After the expression, and sample data have been loaded via the connector module 300, the user can view, query and analyze the user's own data together with the pre-existing data.

The connector architecture preferably is object-oriented so components can be developed and modified individually. Wherever possible, schema-dependent rules and logic are stored outside the code so that schema changes can be readily made without affecting the code. The connector database and server components preferably run on hardware from Sun Microsystems, Inc. (Palo Alto, Calif.) on the Solaris™ 8 Operating Environment (also from Sun Microsystems). The database is preferably Oracle Server 8.1.7.3. Other software includes Visibroker® C++3.3.2 from Borland Software Corporation (Scotts Valley, Calif.), Java 2 SDK version 1.3.1.03 (available on the WWW from Sun Microsystems), Apache HTTP server 1.3.12 and Xerces-c 1.7.0 XML parser (both from Apache Software Foundation, available on the worldwide web at apache.org), Expat 1.95.2 XML parser library (available on the Internet from SourceForge), and Perl 5.6.0 and 5.6.1. For any of the identified software, later versions may be used as well. Supporting documentation for the hardware and each of the listed software programs is incorporated herein by reference for purposes of this disclosure. For more information the exemplary system architecture described above, the reader is referred to commonly-assigned U.S. application Ser. No. 10/090,144, and PCT Application Serial No. US02/19877, which have previously been incorporated herein by reference.

The present invention provides systems and methods for analyzing gene expression, gene annotation, and sample information preferably in a relational format supporting efficient exploration and analysis, including comparative differential expression analysis, expression pattern matching, and mapping of external attributes or identifiers to internal representations of gene fragments or samples. A contrast analysis tool according to a preferred embodiment of the present invention applies a statistical method of contrast analysis in order to prioritize a set of genes according to how well each gene's pattern of expression under different experimental conditions follows any pattern from among a group of user-specified patterns. Another preferred embodiment according to the present invention includes a method and system for improving existing methods for computing gene signature differentials. Yet another preferred embodiment of the invention provides for importing genes or samples by attribute value, providing a mechanism for creating gene sets or sample sets that correspond to some set of values for some attribute or identifier associated with samples or genes in the database.

In a preferred embodiment according to the present invention, the application provides the ability to perform a Contrast Analysis, which is a "pattern matching" tool used to find genes that fit a pattern of expression across sample sets. The specific statistical method is a one-way analysis of variance (ANOVA) model with expression values used as response variables and sample sets used to define groups. One definition of a contrast is a linear combination of group means used to construct a t-statistic for significance testing. The linear combination is specified by a vector of contrast weights. For example, if $\{-1, 2, 1\}$ are the weights, the weights must add to zero (so that t-statistic will be zero if all means are the same). Contrasts are used to specify patterns among group effects. If the groups are labeled A, B, and C, for example, the contrast weight vector $\{1, -2, 1\}$ specifies a null hypothesis of the form:

$H(0)$: $M(A)-2M(B)+M(C)=0$, where $M(x)$ is the mean population for x. (The test is performed on the logarithm of the expression values, not on the expression values directly. This is done to increase the statistical power of the method. Negative expression values are mapped to negative log values by taking the log of the absolute value and multiplying by $-1$. Expression values whose absolute values are less than 1 are replaced by 0. Note that MAS 5 signals, which replace MAS 4 average differences, do not produce any negative values.)

The null hypothesis is used to calculate a t-statistic for each pattern in a method similar to the familiar two-sample t-test, which is well known to those skilled in the art. The value of the t-statistic increases according to the adherence to the pattern of the expression values of the gene over the samples in the sample sets. Large positive t-scores indicate that the pattern of variation of expression values between sample sets, relative to the amount of variation within sample sets, closely follows the pattern represented by the contrast. Large negative t-scores indicate that the pattern of variation is the inverse of the pattern represented by the contrast. This would happen, for instance, for the contrast $\{-1, 1\}$ (representing an increase of expression in Sample Set 2 relative to Sample Set 1) for genes whose expression was decreased in Sample Set 2. Finally, t-scores close to zero indicate that the gene's expression pattern matches neither the contrast pattern nor its inverse, or that the amount of variation between sample sets is comparable to or smaller than the variation within sample sets.

Multiple contrasts can be tested in parallel in order to rank genes according to how well they fit any of several patterns. The user has the option of ranking the genes by either the maximum t-score (corresponding to selecting genes by the best fit to a single pattern) or the minimum t-score (corresponding to selecting genes by their ability to fit all of the patterns).

The contrasts can be specified either by using a graphical tool or by directly entering the contrast weights. Due to the mathematical constraints of the model, some patterns specified by the graphical tool may lead to unexpected results. As described below, in these cases, a warning is issued at the time the pattern is specified, and the user is encouraged to examine the output of the analysis carefully to ascertain that the result generated corresponds to what the user is expecting to obtain.

If requested, a p-value is estimated by a randomization trial over sample assignments to sample sets to assess the significance of the maximum t-score over all the genes and patterns requested.

A tool for detecting outlier samples, which may be referred to as the "Leave One Out Plot,", or LOO method, may also be used, as discussed more fully below. This tool allows the user to identify samples that behave so differently from other members of their sample sets that they have a disproportionate effect on the results of the contrast analysis. These samples can be analyzed further with other tools to determine if there are problems with the sample data quality.

Contrast analysis, as described herein, is related to fold change analysis as disclosed in U.S. application Ser. No. 10/090,144, which has previously been incorporated herein by reference, and operates on multiple groups of sample sets, performing a similar series of fits for each group and comparing their levels using a set of contrasts specified by the user. Once these group effects are calculated, the results are multiplied by the contrasts, and a new statistic is calculated, which is similar in form and meaning to the two-sample t-statistic.

Contrast Analysis can be seen as an extension of fold change analysis. The fold change tool is used to compare expression levels between two experimental conditions, or groups. This tool computes t-scores (not exposed to the user) that can be used to rank the strength of the difference between conditions for an individual gene. These t-scores are the basis of a t-test comparing the difference of the group means against the null hypothesis that the means of the populations sampled by the experiments are equal, taking into account the group variance, and are the input into the algorithm that determines the p-values reported.

Since the logarithms of the data points are taken before the analysis is performed, the fold change is determined based on the ratio of the geometric means of the data in the two groups compared. For sample sets A and B, the t-score is simply the difference between the mean of log transformed expression values for sample set A minus the mean of log transformed expression values for sample set B, divided by the root mean square of the variations of the two logged groups, and weighted by the number of points in each sample set. Take:

m(A)=mean log transformed expression values for sample set A
v(A)=variance log transformed expression values for sample set A
n(A)=number of points in A and define similar values for sample set B. The null hypothesis is given for this test as:

H(0): M(A)−M(B)=0 (i.e., mean in population A is the same as mean in population B. It should be noted that "M" is used to refer to population values, or unknown parameters, while "m" is used for the corresponding sample value computed from the observed data.)

The t-score is given by $$t(A,B)=[m(A)-m(B)]/\sqrt{v(A)/n(A)+v(B)/n(B)}$$

The fold change reported is $\exp(m(A)-m(B))$.

To summarize the t-score calculation, the larger the difference of the log means relative to the log variances, the larger the absolute value of the t-score, and the more likely that the groups actually are different. The null hypothesis for the t test is that M(A)=M(B). When the null hypothesis is true, there are no difference in the populations and the t-statistics computed from the sample data should be small. When the null hypothesis is false, the t-statistic will be different from zero. The higher the t-score, the lower the p-value. The p-value reported by the fold change tool is based on assuming that the log transformed expression values are normally distributed, and the weighting factor takes into account a possible difference in the group sizes. Summarizing an experimental group's characteristics with its estimated mean and variance is a powerful technique for reducing the complexity of analyzing such comparisons.

This idea can be extended to more than two conditions (or groups, or sample sets) using the statistical method of Contrast Analysis, which uses the results of an ANOVA on the individual groups to specify patterns among group effects. Whereas the simple t-test compares two group means, a contrast analysis compares the relative levels of a large number of group means to a model specified by the user. Many situations that arise in the analysis of expression data are amenable to such analysis, if the method is understood properly. However, there are limitations to this method, and care must be taken to understand them to ensure that the results are interpretable. This method is particularly useful when comparing the fits of two or more models to the data. As in the case with the two group t-test, a ranking score (called a t-score, or t-like statistic) is generated that allows a comparison of how well a pattern matches the data. These patterns are parameterized by a contrast (a series of coefficients for the group means).

The input parameters for a contrast analysis include two or more sample sets and a gene set. The user must also specify a set of contrasts, the normalization to use, whether to rank genes by maximum or minimum contrast, and where to compute p-values. The contrasts can be specified either by using a graphical tool or by directly entering the contrast weights. All gene sets selected are combined together to create the input gene set for the analysis; the order of the gene sets is not important.

Since the test relies on the null hypothesis that all group means are the same (that is, there is no difference in expression among the groups), the only valid contrasts are those in which the means are weighted with coefficients that sum to zero. Ranking the genes for the comparisons in decreasing order of t-score should give the same order as ranking the genes in increasing order of p-value.

The contrast analysis tool uses a more sophisticated algorithm to calculate p-values, which algorithm is not based on the assumption that the measurements are normally distributed within groups. Instead, the p-values are calculated by computing a distribution of the maximum t-score over all genes and all patterns. First, the expression values for the different genes are randomly reassigned many times, and the entire set of t-scores is recomputed. The maximum is found for each iteration, and this distribution of t-values is used to estimate the p-value for the maximum t-score reported. The number of mathematically independent contrasts that can be tested against is simply the number of groups (G) minus 1. In the case of the simple t-test, G=2 and only one contrast exists. As G increases, so does the number of independent contrasts. However, any contrast that is a linear combination of these independent contrasts is valid within the theory. Included within the sets of valid contrasts are those which include coefficients equaling zero. These cases require special attention, since a weighting of zero removes that value from the contrast calculation in the numerator of the t-score, while including that group's variance in the denominator.

Figure 3:
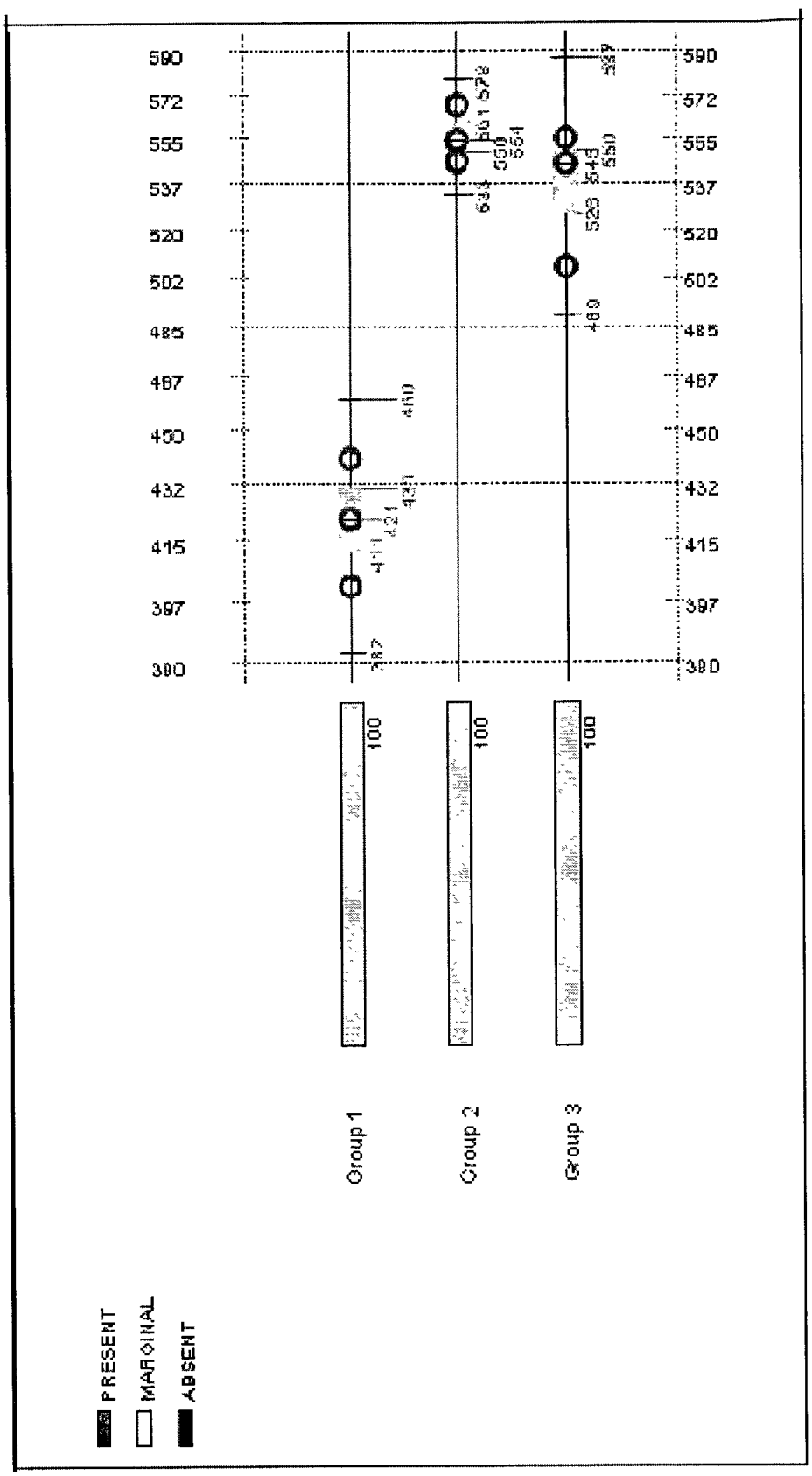
FIG. 3 is an illustration of a contrast analysis.
Figure 4:
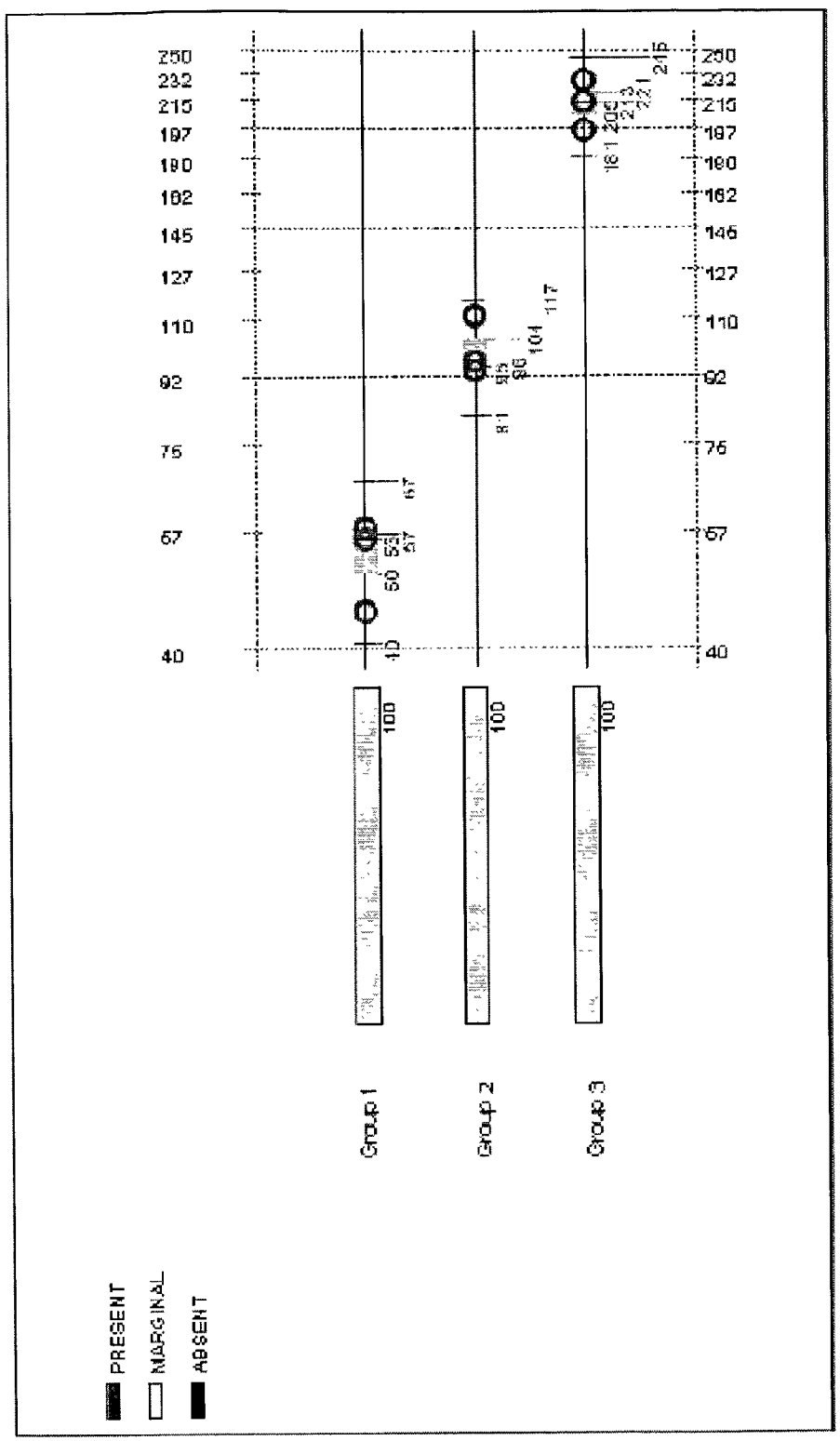
FIG. 4 is an illustration of a contrast analysis.
Figure 5:
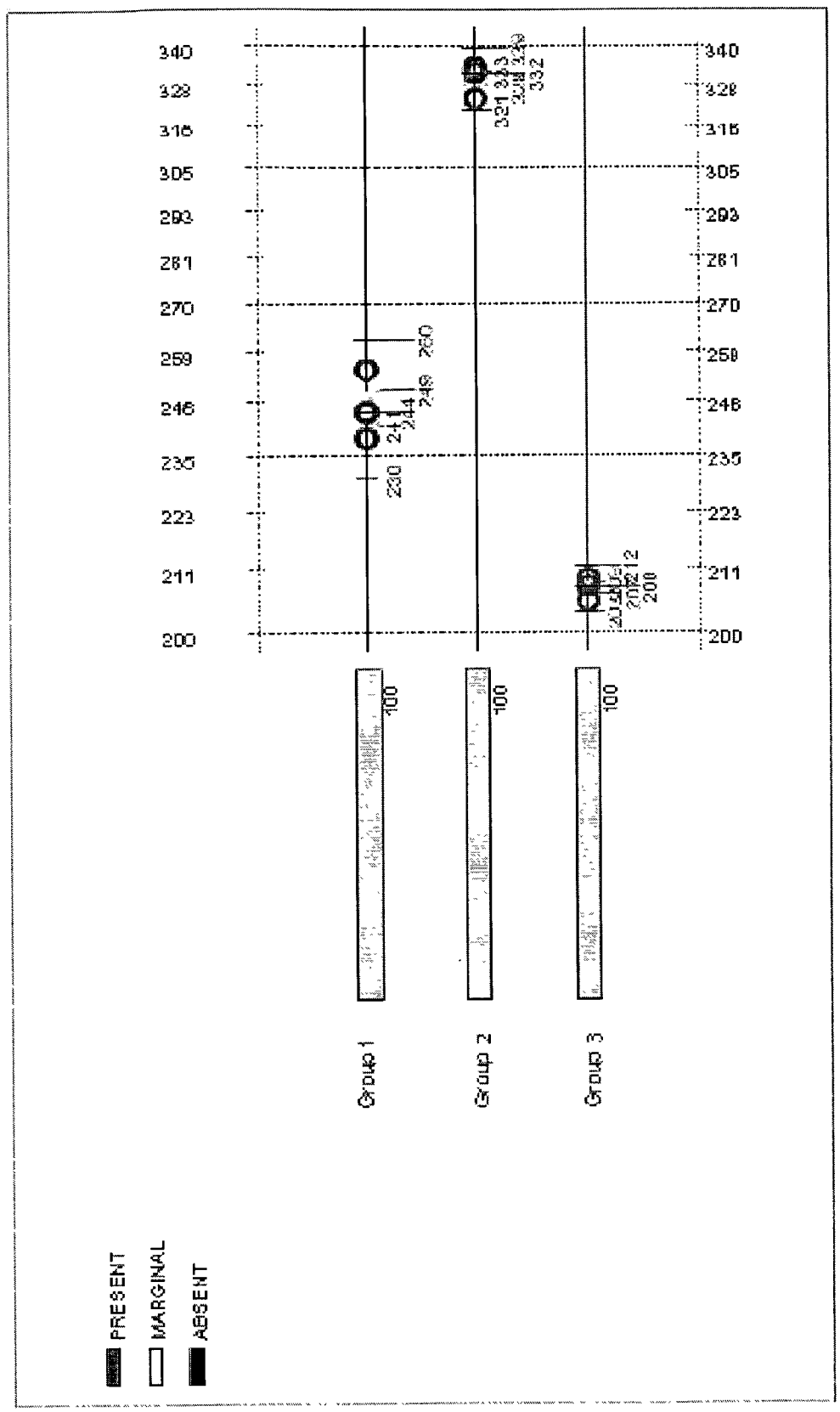
FIG. 5 is an illustration of a contrast analysis.

A simple application of these methods is to rank probe sets by the similarity of their expression pattern to the model(s) specified. Consider a comparison between three groups (Groups 1, 2, and 3) for three Affymetrix® probe sets, as shown in FIGS. 3, 4, and 5, with all plots shown using the log scale. These three figures illustrate different examples of patterns of gene expression. As shown in FIG. 3, Groups 2 and 3 exhibit increased expressions, with Group 2 and 3 expressions approximately the same. In FIG. 4, there is a monotonically increasing expression from Group 1 to Group 2 to Group 3. Finally, as shown in FIG. 5, expression in Groups 1 and 3 are about the same, while Group 2 is more highly expressed than either.

Figure 6:
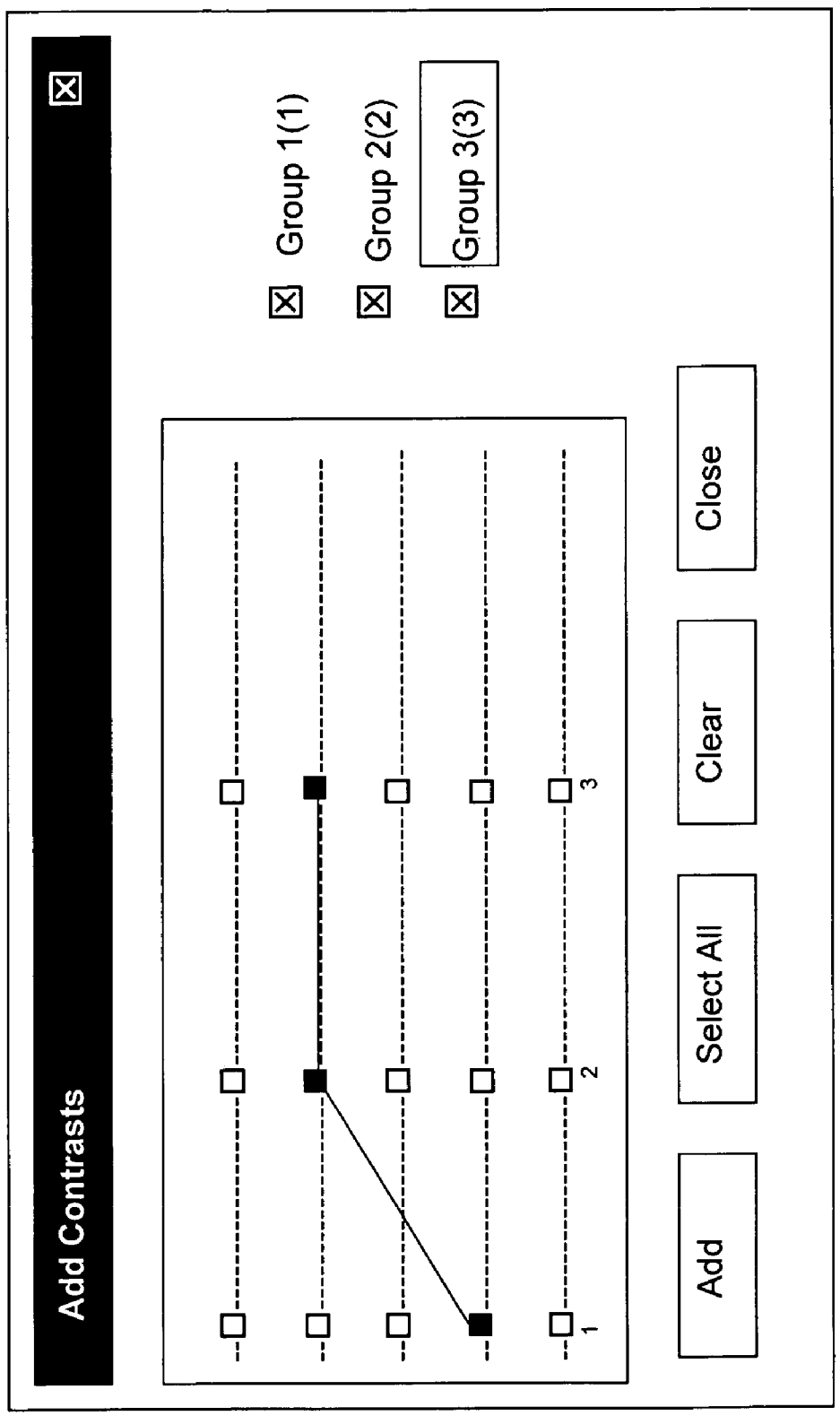
FIG. 6 is an exemplary user-specified contrast pattern.

If one wanted to find the contrast that best describes the situation found in FIG. 3, one would select a contrast pattern that showed Group 1 less than Groups 2 and 3, but with the latter two at the same level, as shown in FIG. 6. The contrast C1 that results is {−2, 1, 1}. The null hypothesis is:

$$H(0): -2*M(1)+M(2)+M(3)=0.$$

The means are defined on the logarithm of the raw expression data. The t-score is:

$$t(1,2,3)=W(C1)*[-2M(1)+M(2)+M(3)]/sqrt[V(1,2,3)].$$

V(1,2,3) is the residual variance from the ANOVA model fit, which depends on the variances of all three groups relative to their respective means, and W is a weighting factor that allows different contrast to be compared to each other. Expressed in terms of there individual group variances, $$V(1,2,3)=[V(1)*(N(1)-1)+V(2)*(N(2)-1)+V(3)*(N(3)-1)]/[N(1)+N(2)+N(3)-3].$$

Regardless of what groups are included in a contrast, the residual variance is obtained from the fit to all study groups selected at the start of the contrast analysis session.

It is important to remember that the contrast depends on the means and the residual variance of the ANOVA fit. The residual variance will be higher, all other things being equal, when the individual group variances are higher for all three groups. The higher the Group 2 and Group 3 means are relative to Group 1, the higher the t-score will be. If the means are all the same, the t-score is close to 0. If the variances are high, for the same group means the t-score will be lower.

An exemplary Contrast Analysis algorithm is as follows:

1. Perform a logarithmic transformation of the data points Eraw, the raw expression values. The transformed values are given by:

E=log(Eraw) for Eraw>1
 =0 for |Eraw|<=1
 =-log(-Eraw) for Eraw<1

2. Generate the X matrix of group assignments. This consists of N rows by K columns, where N is the total number of individual samples, and K is the total number of groups. In the kth column, the nth row contains 1 if the nth sample is in group k, and 0 if not.

3. This matrix is the basis of a family of models (a model is fitted for each gene separately):

$$E=XB+\epsilon$$

where E is a (N X 1) column vector of transformed expression observations for a gene, B is a (K X 1) column vector of parameters, and $\epsilon$ is the residual error, assumed to be normally distributed about 0 with variance $\sigma^2$. If a value is missing in the column vector E (indicated by a "N" or "U" call in the presence call matrix), the value is imputed by the group mean and the residual variance adjusted accordingly. This, in effect, is equivalent to removing the sample from the analysis.

4. Least squares and maximum likelihood estimates of the parameter vector $\beta$ are solutions to the least squares normal equations:

$$X'XeB=X'E$$

Here X' is the transpose of X. Note that the numerical method of solution for this equation is not specified here; there are many methods of solving this equation. The current implementation of the algorithm uses QR decomposition.

5. Let $\beta$ denote the estimate for B (the solution to the normal equations above). An estimate of the variance from the fit is obtained by calculating the mean residual sum of squares:

$$e(\sigma^2)=(E-(\beta X))(E-(\beta X))'/(N-K)$$

6. The comparative t-scores are calculated by using the contrast matrix C, a(K X C) matrix of the C desired contrasts. For each contrast, the cth column consists of a coefficient for the kth group in the kth row. The numerators of the c t-scores are given by the rows of the (1 X C) vector F:

$$F=C\beta$$

The denominators are given by the square root of the rows of the (1 X C) vector V:

$$V=|e(\sigma^2)diag(CInverse(X'X)C')|.$$

Here diag(X) extracts the diagonal elements of a matrix X. It generates a vector of t's whose cth component is given by:

$$T=F/sqrt(V).$$

Note that unlike the case of the fold change t-scores, the assumption made here is of equal variances across groups.

7. If C>1, the maximum or minimum t-score is selected out of the tc's for each gene, depending on the user input for which comparison is desired. The contrast index c is noted for the contrast that satisfies the minimum or maximum criterion.

8. These maximum or minimum t-scores are then combined across all genes to generate a list Tmax or Tmin of length G indicating which patterns are most/least strongly matched. (To simplify further explanation, any reference to Tmax below should be understood to mean either Tmax or Tmin.)

9. If the user has requested p-values, these are generated by a procedure whereby the individual measurements are assigned with replacement to different samples for 1000 trials. For each randomization trial j, calculate the maximum t-score for each g: Tmax(g, j). Take the maximum of all these to generate a top ranking t-score Tmax(j). These are pooled together across all the randomization trials and genes to generate a distribution of maximal t-scores Tmaxpooled. The original t-scores generated in step 8 are compared to their rank in this pooled distribution. Divide the number of points in the pooled distribution with a greater T-value by the total number of points in the pooled distribution to estimate the p-value, that is:

$$p(g)=(\text{number } T\text{maxpooled}>t)/G*1000$$

The Leave One Out Plot involves repeating the contrast computation N times. For each of these N cases, one of the N samples is left out of the calculation and a ranked list, r(g)=rank of g in Tmax, of maximum t-scores is generated. If each gene g has a rank r(g,0) with no samples left out and rank r(g,n) with sample n left out, then compute for each gene the value:

$$d(g,n)=|r(g,n)-r(g,0)|$$

And calculate the median value of d over the user-specified number of genes:

$$d(n)=\text{median}(d(g,n))$$

This value is used as a summary statistic to estimate the effect that leaving one sample out has on the results of the analysis (namely, the ranking of the genes according to the contrasts specified).

In performing a Contrast Analysis, the user first selects sample and gene sets for the analysis. A user selects the sample sets for analysis through the user interface by selecting sample sets displayed on the display screen. It is important to select sample sets that do not have overlapping samples. All gene sets selected will be unioned together for the calculation. Next, the user defines the contrast pattern(s). A preferred method for accomplishing this is to select either highest or lowest for the "T-score among contrasts." Using the maximum T-score (i.e., the highest) to rank genes functions as a logical OR pattern search; that is, genes are ranked high if a large T-score is obtained for any of the input patterns. Alternatively, genes can be ranked by the minimum T-score. This functions as a logical AND on the input patterns, and is useful when the user wants to select for a set of genes that match one or more patterns equally well.

Preferably, there are two ways of defining the contrast patterns: specifying a graphical pattern and entering contrast weights. Specifying a graphical pattern option presents a graphical representation of the contrast pattern that makes it easier to visualize the contrast pattern(s) being used for the analysis. Preferably, the relative direction of the pattern is low, high, or neutral for each of the selected sample sets. The pattern represents the change in mean expression value over each checked sample set. Only the relative vertical order of the values is significant in the pattern. The pattern is converted to a "contrast," which is a list of integer weights, one for each input sample set.

The contrast weights are positive or negative numbers, one for each input sample set, whose values follow the same relative order as the heights of the boxes (i.e., relative vertical order discussed above). The values are scaled and adjusted so that the sum of the weights is zero. Zero weights are assigned for sample sets that are not used in the pattern. All of the sample sets displayed in the contrast analysis window are included in the analysis. For each sample set, a mean and residual are calculated. The residuals from all sample sets are pooled for use in the t-score calculation, regardless of the pattern and whether or not the sample set was selected. This includes samples whose contrast weight is zero. Only the rank order of mean log expression levels between the sample sets is considered when converting the pattern to a contrast. For example, the patterns corresponding to the contrast weight vectors $\{-1, 2, -1\}$ and $\{1, 2, 1\}$ are considered equivalent, although the vectors themselves and their graphical representations are not the same. Simply put, both patterns will select for genes whose mean log expression over Sample Sets 1 and 3 is the same, and is lower than the mean log expression for Sample Set 2.

The correspondence between patterns and contrast vectors is not always so intuitive. A confusing example is the pattern that corresponds to the contrast weight vector $\{-1, 0, 1\}$. This pattern selects for genes whose mean log expression level in Sample Set 1 is lower than that in Sample Set 3. The zero weight for Sample Set 2 means that the mean log expression value over this set is not taken into account. The t-score that results will be independent of the mean log value for the second sample set, contrary to the appearance of the pattern. For this reason, a warning is preferably issued and a warning dialogue may be displayed for the user.

In the entering contrast weights option, an advanced interface is provided to allow for entering the weights directly. The user enters one contrast weight for each sample set. An interface is also provided for the user to select from one of several available expression data normalization methods. A checkbox option is also provided for the user to choose whether or not p-values shall be calculated for the maximum t-scores.

When the contrast analysis computation is complete, the results are displayed in the Results table. Preferably, the genes from the input gene set(s) are sorted in decreasing order of either the maximum or minimum t-score and are presented in a tabular view with columns of the table including the gene attributes selected by the user, a t-score column for each contrast pattern, the maximum and minimum t-score from the t-score columns (if there is more than one contrast), and an index of the maximum t-score (if there is more than one contrast).

Preferably, the contrast analysis aspect of the application of the present invention also provides a Leave One Out Plot. The Leave One Out Plot is a tool for detecting outlier samples and allows the user to identify samples that behave so differently from the other members of their sample sets that they have a disproportionate effect on the results of the contrast analysis. These samples can be analyzed further with other tools to determine if there are problems with the sample data quality or if these samples are unique in some way.

Preferably, the Leave One Out plot provides an interface for the user to select a number N of genes to rank in the analysis. In performing the leave-one-out analysis, the application iterates over the samples in the input sample sets. For each sample, the application removes the sample from its sample set and re-computes the t-scores for all contrasts for the genes that were input to the contrast analysis. The application then re-ranks all the genes by maximum or minimum t-score. Next, for the N genes that are most highly ranked in the original analysis, the application subtracts each gene's original ranking from its new rank and computes the absolute value of the difference. The median of these absolute value differences for the N genes is then computed. Finally, the median is displayed for each input sample as bar graph in the Leave One Out plot.

Samples that behave very differently from the other members of their sample set may be associated with bars that are taller than most of the other bars in the plot. The Leave One Out plot provides the user with the option to temporarily remove one or more of these samples from its input sample set, recompute the contrast analysis, and display a new Leave One Out plot.

One application of the contrast analysis tool is to produce gene ranking for the purpose of identifying singly differentially expressed genes across varieties. A typical toxicology experiment consists of chip data for a number of genomic IDs. Genomic IDs fall in study groups. Dosage and time to sacrifice are typical factors characterizing the different groups. Each study group typically consists of 3, 5, or 10 genomic IDs, plus or minus some losses due to gross experimental error. The contrast analysis tool provides an efficient way to prioritize a large number of genes by comparing gene expression levels and looking for targeted patterns of expression in toxicology studies. The tool can be used to order all genes by the size of the difference in expression level between treated and untreated groups, or by adherence to a given pattern of expression, usually a time course or a particular dose response curve. The tool has other applications such as quality control and gene screening.

When a gene is know in advance (not discovered through ranking), the t-score for that gene may be considered and interpreted by themselves. When a gene is uncovered through the ranking of its t-scores with respect to a set of genes under investigation, to assess the significance of the t-scores the distribution of extreme values in a batch of t-scores similar to those under study must be referenced. A Monte Carlo simulation is used to produce a large number of batches of such t-scores under the null distribution of no group effect and assess significance of t-scores for genes discovered through ranking by comparing the t-scores to extremes of the generated batches.

When a gene is identified though its t-score in relation to the rest of the scores, the statistic used for analysis is not simply the gene specific t-score, but the entire distribution of t-scores for all the genes in the analysis. To assess significance, the repeated sample null distribution of extreme values over the set of t-scores for all the genes in the analysis must be considered. More specifically, the null distribution of extreme values over the set of t-scores will provide a reference distribution against which the significance of any gene identified by the magnitude of its t-score can be assessed.

If a gene is know in advance, significance of its statistics can be assessed in isolation of the other genes. If an assumption of normality or asymptotic approximate normality is made, a table of t distribution may be referred to assess significance. Alternatively, a null distribution of t-scores may be generated for this gene and used for significance assessment. The data can be extracted from the set of replicates generated for other applications.

The main output of the contrast analysis tool is a query result—a ranking of genes from an input gene set, which can be saved for further analysis. Metrics on rankings can be extended to metrics on partial rankings. An extension of Spearman's foot rule to measure distances between partial rankings can be used or a measure of the distance between two rankings is given by the median absolute difference in ranks among the top ranked genes in two rankings.

Genes may be reranked by deleting one chip at a time using some omnibus contrast for ranking, using average or median absolute difference in ranks among top ranked genes. This analysis may point out seriously ill-conditioned chips.

The rankings can be used for further analysis by correlating ranking percentiles of specific genes across studies, to identify problem arrays, to compare model fits, and to assess convergence. Chips that stand out singly must be differentiated from chips which stand out as a group.

Preferably, as viewed through user interface 400, the software for gene expression module 200 provides a variety of menu options that are available for use with the Contrast Analysis, including: a File, New option which opens a new Contrast Analysis window; a File, Open option which allows a previously saved contrast analysis to be opened; a File, Save Contrast Analysis option which allows the contrast analysis to be named and saved; a File, Save Gene Set option which allows the gene fragments currently displayed in the Contrast Analysis results table to be saved as a gene set; a File, Save Selected Genes option which allows selected gene fragments to be saved as a unique gene set; a File, Export option which provides options for exporting the results; a File, Invoke option which provides options for accessing third-party applications in which to view the results; a File, Print option which allows the results to be printed; and a File, Close option which closes the Contrast Analysis window.

Preferably, the Contrast Analysis menu further includes the following: a View, Compute Form option which displays the Compute panel; a View, Results option which displays the Results panel; a View, Show Details Panel option which toggles to the display of the details panel within the Results panel; a View, Select Display Attributes option which opens the Select Display Attributes window where gene attributes and data values can be selected for display in the results table; a View, Gene Set Mask, Add/Remove Mask option which allows a masking gene set to be applied to or removed from the currently displayed result gene set; a View, Gene Set Mask, Remove Selected Genes option which removes the selected genes from the currently displayed result gene set; a View, Gene Set Mask, Remove Unselected Genes option which removes the unselected genes from the result gene set; a View, Gene Set Mask, Reset to Original Gene Set(s) option which resets the result gene set to its original state; a View, Sort By option which sorts the results; and a View, Plot Options option which opens the Plot Options window where the user can select options for a box plot display of the results.

A gene signature analysis computes two sets of gene fragments given a sample set: those that are consistently present within the sample set, and those that are consistently absent. The user specifies the required consistency of expression as two threshold percentages, one for the "present" set, the other for the "absent" set. The result can be thought of as a pair of gene sets. If there are five samples in the sample set, and the threshold percentages are set to 80% and 100%, respectively, then the "present gene set" of the gene signature contains those gene fragments that are present in at least 4 out of 5 samples, while the "absent gene set" contains all gene fragments that are absent in all samples. The displayed results of the gene signature analysis include the total number of fragments in the present and absent sets of the signature plus the threshold percentages.

Gene fragments that have "marginal" calls for a particular sample are treated the same as "absent" fragments. Fragments that have "unknown" calls are ignored in the gene signature computation. If, for a particular gene fragment, p, m, and a are the numbers of samples for which the fragment was present, marginal, and absent, respectively, then the fractions $p/(p+m+a)$ and $(m+a)/(p+m+a)$ are computed. These fractions are compared against the present and absent threshold percentages to determine if the fragment belongs to either of the gene signature gene sets.

In another preferred embodiment of the present invention, the application can perform a gene signature differential analysis. A gene signature differential analysis identifies differentially expressed gene fragments by comparing the results of two gene signature analyses on different sample sets which have been previously computed and saved. The gene signature analysis generates two sets of gene fragments given a sample set: a "present" gene set that includes those fragments with detectable expression in more than a user-specified fraction P of samples in the sample set, and an "absent gene set" that includes those fragments without detectable expression in at least a user-specified fraction A of samples in the sample set. Using the present and absent gene sets for the first and second gene signatures, the gene signature differential analysis derives the following four new sets of gene fragments: 1) those that are in both gene signature's present gene sets; 2) those that are in both gene signature's absent gene sets; 3) those that are in both the first gene signature's present gene set and the second gene signature's absent gene set; and 4) those that are in both the first gene signature's absent gene set and the second gene signature's present gene set.

To compute a gene signature differential, the user selects two gene signature results that he or she wishes to compare from the listed results on the workspace page. The results are summarized in a table such as the following example:

| Gene Signature Differential computed on | |
|---|---|
| Gene Signature Results 1 | 80% GeneSig of Livers-hepatocellular carcinoma<br>P1 has 7398 gene items<br>A1 has 23626 gene items |

-continued

| Gene Signature Differential computed on | |
|---|---|
| Gene Signature Results 2 | 80% GeneSig of Normal livers<br>P2 has 3948 gene items<br>A2 has 27390 gene items |

| Intersection Gene Sets | Affy Fragment Count |
|---|---|
| P1 intersect A2 | 23 |
| A1 intersect P2 | 0 |
| P1 intersect P2 | 3700 |
| A1 intersect A2 | 22819 |

P1 and A1 refers to the Present and Absent Gene Set of Gene Signature 1 respectively;

P2 and A2 refers to the Present and Absent Gene Set of Gene Signature 2 respectively.

Gene expression measurements are obtained from experiments using gene chip microarrays to profile expression in tissue or cell culture samples of tens of thousands of genes simultaneously. For each sample and each gene, the technology produces a "call value" which may be one of the following: (1) present/detected or "P"; (2) absent or "A"; or (3) marginal or "M". "Present" means the gene has detectable expression in the sample, "absent" means it does not. There are two other possible call values: unknown or "U", meaning an erroneous or unreliable measurement; and null or "N", meaning that expression was not measured for the gene and sample in question. Samples with U or N calls are not counted when the gene signature analysis computes ratios of sample counts and compares them against the threshold fractions. For more information on the gene signature algorithm, the reader is referred to U.S. application Ser. No. 10/090,144, which has previously been incorporated herein by reference.

Let $SS_1$ and $SS_2$ be disjoint sets of samples. Let $Tp_1$, $Ta_1$, $Tp_2$, and $Ta_2$ be arbitrary threshold fractions between zero and one. Let $P_k$ be the set of genes analyzed that are called "present" in at least $Tp_k*N(SS_k)$ samples of sample set k, where $N(SS_k)$ is the number of samples in $SS_k$. Let $A_k$ be the set of genes that are called absent or marginal in at least $Ta_k*N(SS_k)$ samples of sample set k. The purpose of the gene signature differential analysis is to calculate the two sets of genes $P_1 \cap A_2$ (the "PA set") and $P_2 \cap A_1$ (the "AP set") in an efficient manner. Most genes analyzed in the microarray experiments do not belong to the PA or AP sets.

Although it may be necessary to count the P, A, and M calls from most or all samples to confirm that a gene belongs to one or the other set (because the unknown and null calls are not counted in computing the fractions that are compared against the thresholds), it is typically necessary to count only a fraction of the calls to be sure that the gene does not belong to either set. The fraction is smaller the closer the threshold fractions are to one.

If one sample set is much larger than the other, efficiency is increased by performing tests on the smaller sample set first. For example, suppose sample sets $SS_1$ and $SS_2$ have 500 and 10 samples, respectively, and the present and absent threshold fractions are 0.8 for both sets. For a gene g, the analysis includes iteration over the samples in the smaller set, $SS_2$, first, counting P, A, and M calls. Once three P calls are recognized, it is known that g is not in the PA set (i.e., because gene g is not in the absent set of $SS_2$). The fraction Na/(3+Na), where Na is the number of samples with A or M calls for gene g, will be 0.7 or less (unknowns and nulls make it less) regardless of how many A calls are obtained from the rest of the samples. Similarly, once three A calls are recognized, g is excluded from the AP set (i.e., because gene g cannot be in the present set of $SS_2$).

Stated more formally, if the running count Np of present calls is greater than $(1-Ta)*NSS$, where Ta is the absent threshold and NSS is the size of the sample set, then the gene is excluded from the sample set's absent set. If the count of absent and marginal calls Nam is greater than $(1-Tp)*NSS$, then the gene is excluded from the present set.

According to a preferred embodiment of the gene signature differential analysis, the gene sets $P_1 \cap P_2$ (the "PP set") and $A_1 \cap A_2$ (the "AA set") not calculated unless the user specifically requests that this be done, thus greatly increasing the efficiency of the process. Only the sets representing the differences (i.e., the PA and AP sets) are calculated in the gene signature differential analysis. Additionally, past methods of gene signature differential analysis have used two gene signatures as input, as discussed in more detail in U.S. application Ser. No. 10/090,144, but a preferred embodiment of the gene signature differential analysis allows for calculation of gene signature differentials directly from a pair of input sample sets.

There are preferably several components of presentation of the results of the gene signature differential analysis, including the names of the two input sample sets, the size of the sample sets used, and the thresholds used to compute the gene signature differentials; a table summarizing the number of gene fragments in the two present sets: present only in <Sample Set 1>, present only in <Sample Set 2>; and a History panel that records the date and time of the analysis and the version of the analysis engine used. Detailed information about the gene fragment sets for the data the user has selected are preferably displayed in the Gene Set Results panel. Optionally, the following may also be included: an option that displays gene fragments that are present in both sample sets; an option that displays gene fragments that are absent in both sample sets; and a statement of the number of rows in the results and the type of normalization used.

Preferably, if the Show Details Panel option is selected in the View menu, a details panel will be displayed. This panel contains views that display detailed information about selected genes, including gene fragment and known gene attributes, a table of other gene fragments belonging to the same UniGene sequence cluster as a selected fragment, and a box plot display of expression data for one ore more selected gene fragments.

Preferably one can further refine the data content of the Gene Set Results option by selecting viewing options. These options include Show Affy Fragments only, which, if selected, displays user-specified attributes of qualified gene fragments; Aggregate (per sample set) Values, which, if selected, also displays expression value statistics for each gene fragment; Expression and Call values (one row per gene), which, if selected, displays one row per gene that contains the present/absent call and quantitative expression value for the fragment across all samples in the sample set; and Expression and Call values (one row per gene per sample), which, if selected, displays one row per fragment per sample including the actual present/absent call and the quantitative expression value for the fragment for each sample in the input sample sets.

The results of a gene signature differential analysis may preferably be saved for later use. It is also preferably possible to save any or all of the resulting sets as unique gene sets so that such unique gene sets can then be used in conjunction with other analyses and analytical tools.

The gene signature differential menu includes a variety of menu options, including: a File, New option which opens a new gene signature differential analysis window; a File, Open option which allows a previously saved gene signature differential to be opened; a File, Save GS Differential option which allows the gene signature differential to be saved; a File, Save Gene Sets option which allows the individual result gene sets to be saved; a File, Save Selected Genes option which allows gene fragments selected in the table to be saved as a unique gene set; a File, Export option which provides options for exporting the results; a File, Invoke option which provides options for accessing third-party applications in which to view the results; a File, Print option which allows the results to be printed; and a File, Close option which closes the Gene Signature Differential Analysis window.

The gene signature differential menu options preferably also include: a View, Compute Form option which displays the Compute panel; a View, Summary option which displays the Summary panel; a View, Gene Set Results option which displays the Gene Set Results panel; a Pathway Viewer option which displays the Pathway Viewer panel; a Chromosome Viewer option which displays the Chromosome Viewer panel (Pathway and Chromosome Viewers are discussed in detail in U.S. application Ser. No. 10/090,144); a Show Details Panel option which toggles the display of the Details panel within the Results panel; a View, Select Display Attributes option which opens the Select Display Attributes window; a View, Gene Set Mask, Add/Remove Mask option which allows a masking gene set to be applied to or removed from the currently displayed result gene set; a View, Gene Set Mask, Remove Selected Genes option which removes the selected genes from the currently displayed result gene set; a View, Gene Set Mask, Remove Unselected Genes option which removes the unselected genes from the result gene set; a View, Gene Set Mask, Reset to Original Gene Set(s) option which resets the result gene set to its original state; a View, Sort By option which sorts the results; and a View, Plot Options option which opens the Plot Options window where the user can select options for a box plot display of the results.

Another preferred embodiment of the application according to the invention provides a tool for querying a gene sequence database using multiple queries by permitting a user to create a file containing a list of the multiple attributes for the query. The gene query tool permits a user to import genes or samples by attribute value, providing a mechanism for creating gene sets or sample sets that correspond to some set of values for an attribute or identifier associated with samples or genes in the database, where such attributes have been previously saved in a user-created text file. The result of the import is a list of all samples or gene fragments whose values for the specified attribute match any of the values in the file. Preferably, the sample set or gene set can be saved to be reviewed at a later date or for use with available analyses and analytical tools. During the save process, the sample set or gene set is given a name and permissions may be set to limit who has access to the file. Once saved, the contents of the results do not change, even when more genes that satisfy the query are added to the database. In order to make the gene set current, it is necessary to re-run the query. If the user wishes to retain the original results, the user may save the new results under another name.

The gene query tool may include a dialog box that displays a preview of the different attributes stored in the database for genes or samples from which the user may select an attribute. The dialog box may also provide means for the user to navigate to or enter a name of a file containing potential values for the selected attribute.

In an exemplary embodiment, import by attribute allows for importing gene fragments based on a list of values for a specific attribute. The GenBankID import is a special case where gene fragments can be imported according to the values of the Exemplar Seq: Accession attribute; however, it should be understood that the user can choose any attribute to import by, such as Fragment ID, Fragment Type, Fragment Name, species, BLAST hits, Known Gene: Symbol, and others. The import by attribute aspect of the present invention is also applicable to sample queries. An import dialog can include a display of a query attribute tree. To specify the attribute(s) of the data to be imported, the user navigates through the tree to the desired attribute and selects it. For example, if the user is interested in researching one or more diseases, he or she can request all samples derived from patients by selecting the diseas(es) of interest as the attribute. Once the import has occurred, the results of the import can be saved as a gene set or sample set. Thus, the import by attribute tool may be part of a sample set or gene set query tool of the application. Exemplary sample set and gene set query tools are described in U.S. application Ser. No. 10/090,144.

The foregoing description of the preferred embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the preferred embodiments described therein.

The invention claimed is:

1. A method of analyzing gene expression data comprising:
   providing a data warehouse comprising a plurality of databases for storing data including quantitative gene expression data obtained from microarray analysis of gene fragments, sample data corresponding to tissues or cell lines from which the gene fragments were derived, and gene annotation data corresponding to the gene fragments for uniquely identifying the gene expression data;
   providing an analysis engine for analysis of data in the data warehouse;
   providing a user interface for submitting search queries to the analysis engine and for receiving search results;
   receiving a first search query comprising a first sample set;
   correlating the first search query with its corresponding gene expression data;
   performing a first gene signature analysis to identify gene fragments that have gene expression responses within at least one user-specified threshold;

receiving a second search query comprising a second sample set;

correlating the second search query with its corresponding gene expression data;

performing a second gene signature analysis to identify gene fragments that have gene expression responses within the at least one user-specified threshold; and performing a gene signature differential analysis by comparing the first and second gene signature analyses to identify at least two sets of differentially expressed gene fragments;

wherein the at least one user-specified threshold comprises a selected percentage of a total number of samples in each sample set.

2. The method of claim 1, wherein the gene expression responses comprise consistently present expression and consistently absent expression, and wherein the at least two sets of differentially expressed gene fragments include a first set of differentially expressed gene fragments having consistently present expression in the first gene signature analysis and consistently absent expression in the second gene signature analysis and a second set of differentially expressed gene fragments having consistently absent expression in the first gene signature analysis and consistently present expression in the second gene signature analysis, wherein consistently present expression is determined by a first user-specified threshold comprising a first selected percentage of a total number of samples in each sample set for which expression is present, and wherein consistently absent expression is determine by a second user-specified threshold comprising a second selected percentage of the total number of samples in each sample set for which expression is absent.

3. The method of claim 1, further comprising displaying results of the gene signature differential analysis at the user interface.

4. The method of claim 3, wherein displaying results comprises providing a pathway viewer for displaying gene expression data for the differentially expressed gene fragments overlaid on known pathways.

5. The method of claim 3, wherein displaying results comprises providing a chromosome display for mapping the gene expression data for the differentially expressed gene fragments to a corresponding location on a chromosome.

6. The method of claim 1, wherein the search queries comprise sample data that were imported by one or more user-selected attribute.

7. The method of claim 6, wherein the attribute comprises GenBank ID or a known gene symbol.

8. The method claim 6, wherein the attribute comprises gene fragment type or gene fragment name.

9. The method of claim 6, wherein the attribute comprises disease of interest.

10. A method of analyzing gene expression data comprising:

providing a data warehouse comprising a plurality of databases for storing data comprising quantitative gene expression data obtained from microarray analysis of gene fragments, sample data corresponding to tissues or cell lines from which the gene fragments were derived, and gene annotation data corresponding to the gene fragments for uniquely identifying the gene expression data;

providing an analysis engine for analysis of data in the data warehouse;

providing a user interface for submitting search queries to the analysis engine and for receiving search results;

receiving a first search query comprising a first one of a gene set comprising gene annotation data or a sample set comprising sample data;

receiving a second search query comprising a second one of a gene set comprising gene annotation data or a sample set comprising sample data;

correlating the first and second search queries with their corresponding gene expression data; and performing a contrast analysis to test for patterns of expression within the search queries, the contrast analysis comprising:

applying a one-way analysis of variance (ANOVA) model to the gene expression data, wherein the gene expression data are response variables and the search queries define groups, wherein contrasts are used to specify a pattern among group effects comprising conditions whose effect on gene expression is to be assessed;

constructing a null hypothesis using the pattern among group effects;

generating a t-score for measuring deviation of each gene fragment from the null hypothesis; and ranking the gene fragments according to their t-scores.

11. The method of claim 10, wherein performing the contrast analysis further comprises performing a Leave-One-Out analysis to identify outliers.

12. The method of claim 10, further comprising the steps of:

prior to performing contrast analysis, receiving one or more additional search queries; and correlating the additional search queries with their corresponding gene expression data;

wherein the additional search queries are included in the contrast analysis.

13. The method of claim 10, wherein performing the contrast analysis further comprises:

receiving a user-defined contrast pattern.

14. The method of claim 13, wherein the contrast pattern is defined by a specified graphical pattern or entered contrast weights.

15. The method of claim 13, wherein performing the contrast analysis further comprises logarithmically transforming the gene expression data prior to applying the one-way analysis of variance.

16. The method of claim 13, wherein receiving the user-defined contrast pattern comprises selecting one of a highest or lowest t-score for ranking.

17. The method of claim 10, wherein the search queries comprise gene annotation data or sample data that were imported by one or more user-selected attribute.

18. The method of claim 17, wherein the attribute comprises GenBank ID or a known gene symbol.

19. The method claim 17, wherein the attribute comprises gene fragment type or gene fragment name.

20. The method of claim 17, wherein the attribute comprises disease of interest.

21. A method of analyzing gene expression data comprising:

providing a data warehouse comprising a plurality of databases for storing data comprising quantitative gene expression data obtained from microarray analysis of gene fragments, sample data corresponding to tissues or cell lines from which the gene fragments were derived, and gene annotation data corresponding to the gene fragments for uniquely identifying the gene expression data;

providing an analysis engine for analysis of data in the data warehouse;

providing a user interface for submitting search queries to the analysis engine and for receiving search results;

receiving a first search query comprising a first one of a gene set comprising gene annotation data or a sample set comprising sample data;

receiving a second search query comprising a second one of a gene set comprising gene annotation data or a sample set comprising sample data;

correlating the first and second database queries with their corresponding gene expression data;

performing a contrast analysis to test for patterns of expression within the search queries, the contrast analysis comprising:

applying a one-way analysis of variance (ANOVA) model to the gene expression data, wherein the gene expression data are response variables and the search queries define groups, wherein contrasts are used to specify a pattern among group effects comprising conditions whose effect on gene expression is to be assessed;

constructing a null hypothesis using the pattern among group effects;

generating a t-score for measuring deviation of each gene fragment from the null hypothesis; and ranking the gene fragments according to their t-score;

performing a first gene signature analysis to identify gene fragments that have gene expression responses within a least one user-specified threshold;

performing a second gene signature analysis to identify gene fragments that have gene expression responses within the at least one user-specified threshold; and performing a gene signature differential analysis by comparing the first and second gene signature analyses to identify at least two sets of differentially expressed gene fragments;

wherein the at least one user-specified threshold comprises a selected percentage of a total number of samples in each gene set or sample set.

22. The method of claim 21, wherein receiving a search query comprises gene annotation data or sample data that were imported by one or more user-selected attribute.

23. The method of claim 22, wherein the attribute comprises GenBank ID or a known gene symbol.

24. The method claim 22, wherein the attribute comprises gene fragment type or gene fragment name.

25. The method of claim 22, wherein the attribute comprises disease of interest.

26. The method of claim 21, wherein performing the contrast analysis further comprises:

receiving a user-defined contrast pattern.

27. The method of claim 21, wherein performing the contrast analysis further comprises performing a Leave-One-Out analysis to identify outliers.

28. The method of claim 21, wherein the gene expression responses comprise consistently present expression and consistently absent expression, and wherein the at least two sets of differentially expressed gene fragments include a first set of differentially expressed gene fragments having consistently present expression in the first gene signature analysis and consistently absent expression in the second gene signature analysis and a second set of differentially expressed gene fragments having consistently absent expression in the first gene signature analysis and consistently present expression in the second gene signature analysis, wherein consistently present expression comprises a first user-specified threshold comprising a first selected percentage of a total number of samples in each sample set for which expression is present, and wherein consistently absent expression comprises a second user-specified threshold comprising a second selected percentage of the total number of samples in each sample set for which expression is absent.

29. The method of claim 21, further comprising displaying results of the gene signature differential analysis at the user interface.

30. The method of claim 29, wherein displaying results comprises providing a pathway viewer for displaying gene expression data for the differentially expressed gene fragments overlaid on known pathways.

31. The method of claim 29, wherein displaying results comprises providing a chromosome display for mapping the gene expression data for the differentially expressed gene fragments to a corresponding location on a chromosome.

32. The method of claim 21, wherein performing the contrast analysis further comprises logarithmically transforming the gene expression data prior to applying the one-way analysis of variance.

33. The method of claim 21, further comprising the steps of:

prior to performing contrast analysis, receiving one or more additional search queries; and correlating the additional search queries with their corresponding gene expression data;

wherein the additional search queries are included in the contrast analysis.

* * * * *